(12) United States Patent
Thomas et al.

(10) Patent No.: US 7,820,807 B2
(45) Date of Patent: Oct. 26, 2010

(54) GENE CONSTRUCTS CODING FOR CD40-BINDING ACTIVATING ANTIBODIES

(75) Inventors: David Thomas, Houston, TX (US); Mark De Boer, Blaricum (NL); Pieter C. J. M. Res, Haarlem (NL); Peter J. Simons, Hillegom (NL)

(73) Assignee: Pangenetics BV, Ultrecht (NL)

( * ) Notice: Subject to any disclaimer, the term of this patent is extended or adjusted under 35 U.S.C. 154(b) by 0 days.

(21) Appl. No.: 12/420,481

(22) Filed: Apr. 8, 2009

(65) Prior Publication Data

US 2009/0311268 A1    Dec. 17, 2009

Related U.S. Application Data

(62) Division of application No. 11/613,409, filed on Dec. 20, 2006, now Pat. No. 7,547,438, which is a division of application No. 09/773,866, filed on Feb. 1, 2001, now Pat. No. 7,172,759.

(60) Provisional application No. 60/178,934, filed on Feb. 1, 2000.

(51) Int. Cl.
*C12N 15/13* (2006.01)
*C12N 15/12* (2006.01)
*C12N 5/10* (2006.01)

(52) U.S. Cl. ............... 536/23.53; 536/23.1; 536/23.5; 435/252.3; 435/326; 435/334; 435/343; 435/343.1

(58) Field of Classification Search ............ None
See application file for complete search history.

(56) References Cited

U.S. PATENT DOCUMENTS

| | | | |
|---|---|---|---|
| 4,946,778 A | 8/1990 | Ladner et al. | |
| 5,225,539 A | 7/1993 | Winter | |
| 5,463,564 A | 10/1995 | Agrafiotis et al. | |
| 5,534,254 A | 7/1996 | Huston et al. | |
| 5,585,089 A | 12/1996 | Queen et al. | |
| 5,674,492 A | 10/1997 | Armitage et al. | |
| 5,693,761 A | 12/1997 | Queen et al. | |
| 5,693,762 A | 12/1997 | Queen et al. | |
| 5,723,322 A | 3/1998 | Guettler et al. | |
| 5,801,227 A | 9/1998 | Fanslow, III et al. | |
| 5,901,069 A | 5/1999 | Agrafiotis et al. | |
| 6,106,835 A | 8/2000 | Chang | |
| 6,497,876 B1 | 12/2002 | Maraskovsky et al. | |
| 6,632,992 B2 | 10/2003 | Hasegawa | |
| 7,172,759 B2 * | 2/2007 | Thomas et al. | 424/153.1 |
| 7,547,438 B2 * | 6/2009 | Thomas et al. | 424/153.1 |
| 2003/0022860 A1 | 1/2003 | Melief et al. | |

FOREIGN PATENT DOCUMENTS

WO    99/61057    12/1999

WO    02/11763 A1    2/2002

OTHER PUBLICATIONS

Orkin et al., "Report and Recommendation of the Panel to Assess the NIH Investment in Research on Gene Therapy", NIH, 1995.*

Skolnick et al., Trends in Biotech., 18: 34 39, 2000.*

Eck et al., Gene-Based Therapy, In: The Pharmacological Basis of Therapeutics, Goodman and Gilman, Eds., 1996, pp. 77-101.*

Verma et al., Nature 389: 239-242, 1997.*

Bjorck, P. et al.; "CD40 Antibodies Defining Distinct Epitopes Display Qualitative Differences in Their Induction of B-Cell Differentiation", Immunology, Blackwell Scientific Publications, GB, vol. 87, pp. 291-295, 1996. XP002930984 ISSN: 0019-2805.

Challa, A. et al.; "Epitope-dependent Synergism and Antagonism Between CD40 Antibodies and Soluble CD40 Ligand for the Regulation of CD23 Expression and IgE Synthesis in Human B Cells"; Allergy (Copenhagen), vol. 54, No. 6, pp. 576-583; Jun. 1999. XP002276806 ISSN: 0105-4538.

Dullforce, P. et al.; "Enhancement of T Cell-Independent Immune Responses In Vivo by CD40 Antibodies"; Nature Medicine Natu re Publishing Co., US, vol. 4, No. 1, pp. 88-91; Jan. 1998. XP009026323 ISSN: 1078-8956.

French, R. et al.; "CD40 Antibody Evokes a Cytotoxic T-cell Response That Eradicates Lymphoma and Bypasses T-cell Help"; Nature Medicine, Nature Publishing, CO, US, vol. 5, No. 5, pp. 548-553; May 1999. XP002159390 ISSN: 1078-8956.

Jeffrey A. Ledbetter, et al.; "Agonistic Activity of a CD40-Specific Single-Chain Fv Constructed From the Variable Regions of mAb G28-5"; Critical Reviews in Immunology, vol. 17, Issue 1, pp. 427-435; 1997.

Zhao-hua Zhou et al.; "An Agonist Anti-Human CD40 Monoclonal Antibody that Induces Dendritic Cell Formation and Maturation and Inhibits Proliferation of a Myeloma Cell Line"; Hybridoma, vol. 18, No. 6, pp. 471-478; 1999.

Zhao-hua Zhou et al.; "The obtaining of an anti-human CD40 monoclonal antibody with special functions and the analysis of its biological effects"; Chinese Journal of Immunology, vol. 15, No. 12, pp. 529-533; 1999.

Hilkens, C. M. U. et al.: "Human Dendritic Cells Require Exogenous Interleukin-12-Inducing Factors to Direct the Development of Naive T-Helper Cells Toward the TH1 Phenotype"; Bllod, vol. 90, No. 5 Sep. 1, 1997: pp. 1920-1926.

(Continued)

*Primary Examiner*—Phillip Gambel
(74) *Attorney, Agent, or Firm*—Hoffmann & Baron, LLP (57) ABSTRACT

Disclosed are agonist anti-CD40 molecules, including monoclonal antibodies, which can bind to and stimulate professional and non-professional human antigen-presenting cells ("APCs"), enhance the stimulatory effect of CD40L on CD40 positive cells and/or induce phenotypical maturation of monocyte derived dendritic cells. Several such monoclonal antibodies are provided, and cell lines producing them have been deposited at the American Type Culture Collection.

6 Claims, 10 Drawing Sheets

OTHER PUBLICATIONS

Pound, J.D. et al.; "Minimal cross-linking and epitope requirements for CD40-dependent suppression of apoptosis contrast with those for promtion of the cell cycle and homotypic adhesions in human B cells" International Immunology, vol. 11, No. 1, pp. 11-20.

Bjorck et al. "Antibodies to distinct epitopes on the CD40 molecule co-operate in stimulation and can be used for the detection of soluble CD40." Immunoloav. Nov. 1994;83(3):430-7.

Heath et al. "Monoclonal antibodies to murine CD40 define two distinct functional epitopes." Eur. J. Immunol. 1994; 24 (8):1828-34.

Holder et al. "Suppression of apoptosis in normal and neoplastic human B lymphocytes by CD40 ligand is independent of Bcl-2 induction." Eur. J. Immunol. Sep. 1993; 23(9):2368-71.

Pellat-Deceunynck et al. "CD11a-CD18 and CD102 interactions mediate human myeloma cell growth arrest induced by CD40 stimulation." Cancer Res. Apr. 15, 1996;56(8):1909-16.

Schwabe et al. "Modulation of soluble CD40 ligand bioactivity with anti-CD40 antibodies." Hybridoma. Jun. 1997;16 (3):217-26.

Valle et al. "Activation of human B lymphocytes through CD40 and interleukin 4." Eur. J. Immunol. Aug. 1989;19 (8):1463-7.

Guerder et al., "A fail-safe mechanism for maintaining self-tolerance", J. Exp. Med.176(2):553-564 (1992).

Bennett, S.R.M., et al., "Help for Cytotoxic T-Cell Responses is Mediated by CD40 Signaling", Nature 393:478-480 (1998).

Schoenberger, S.P. et al., "T-Cell Help for Cytotoxic T-Lymphocytes is Mediated by CD40-CD40L Interactions", Nature 393:480-483 (1998).

Armitage, R.J., "Tumor necrosis factor receptor superfamily members and their ligands", Curro Opin. Immunol. 6 (3):407-13 (1994).

Alderson, et al., "CD40 expression by human monocytes: regulation by cytokines and activation of monocytes by the ligand for CD40", .J. Exp. Med. 178(2):669-674 (1993).

Caux, et al., "B70/B7-2 is identical to CD86 and is the major functional ligand for CD28 expressed on human dendritic cells", J Exp Med. 180(5):1841-1847 (1994).

Riechmanna, L., et al., "Reshaping Human Antibodies for Therapy", Nature 332: 323-327(1988).

Evans M. J., et al., "Rapid Expression of an Anti-Human C5 Chimeric Fab Utilizing a Vector That Replicates in COS and 293 Cells", J. Immunol. Meth. 184: 123-138 (1995).

Tang, A. et al., "Suppression of Murine Allergic Contact Dermatitis by CTLA41g: Tolerance Induction of Th2 Responses Requires Additional Blockade of CD-40 Ligand", J. Immunol. 157:117-125 (1996).

Ridge, J. P. et al., "A Conditioned Dendritic Cell Can Be a Temporal Bridge Between a CD4+ T-Helper and a T-Killer Cell", Nature 393:474-477 (1998).

Caux, C. et al., "Activation of human dendritic cells through CD40 cross-linking" J Exp Med. 180(4):1263-1272 (1994).

Ngo et. al: "Computational Complexity, Proteing Structure Prediction, and the Levinthal Paradox" The Protein Folding Problem and Tertiary Structure Prediction. 1994 pp. 433, 492-495.

Skolnick et al.: From Genes to Protein Structure and Function: Novel Applications of the Commutational Approaches in the Genomic Era Trends in Biotech. 18:34-39 (2000).

Kuntz et al.: "Structure-based Strategies for Drug Design and Discovery" Science 257: 1078-1082 (1992).

Caux et al.: "Functional CD40 on B lymphocytes and Dendritic Cells" Research in Immunology 145(3):235-239 (1994).

Katira et al.: "B10.4 Identification for Co-operative Epitopes on CD40 Supports the Existence of a Second CD40 Ligand" In Leukocyte Typing V, Oxford University Press 1995, p. 554.

* cited by examiner

SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence -continued

```
<220> FEATURE:
<223> OTHER INFORMATION: Peptide couplers

<400> SEQUENCE: 1

Gly Gly Gly Gly Cys
 1               5

<210> SEQ ID NO 2
<211> LENGTH: 11
<212> TYPE: PRT
<213> ORGANISM: Artificial Sequence
<220> FEATURE:
<223> OTHER INFORMATION: Peptide couplers

<400> SEQUENCE: 2

His His His His His His Gly Gly Gly Gly Cys
 1               5                  10
```

GENE CONSTRUCTS CODING FOR CD40-BINDING ACTIVATING ANTIBODIES

RELATED APPLICATIONS

This application is a divisional patent application of U.S. patent application Ser. No. 11/613,409, filed on Dec. 20, 2006, now U.S. Pat. No. 7,547,438, which is a divisional of U.S. patent application Ser. No. 09/773,866, filed on Feb. 1, 2001, now U.S. Pat. No. 7,172,759, which claims priority to U.S. Provisional Application Ser. No. 60/178,934, filed on Feb. 1, 2000, all of which are hereby incorporated by reference in their entirety.

FIELD OF THE INVENTION

This invention relates to a series of novel molecules and monoclonal antibodies that bind to and stimulate antigen presenting cells via the CD40 receptor expressed on such antigen presenting cells.

BACKGROUND OF THE INVENTION

Activation of the Immune System

The immune system is capable of killing autologous cells when they become infected by virus or when they transform into cancer cells. Such a potentially dangerous mechanism is under tight control. When they have not yet encountered their specific antigen, the immune system's T-killer cells (CTL) circulate as inactive precursors. To be activated, the precursor T-killer cell must recognize its specific antigen peptide, presented by MHC class I molecules on professional antigen presenting cells (APC). This antigen specific cellular interaction is, however, not enough to fully activate the CTL, notwithstanding the co-stimulatory signals from the APC.

Until recently it was believed that a T-helper cell that recognises the same antigen on the same APC as the CTL is needed to fully activate the CTL. Upon activation, the specific T-helper cell would supply cytokines such as IL-2 needed for the activation of the CTL. Guerder and Matzinger (J. Exp. Med. 176:553 (1992)), however, proposed the "licensing" model for CTL activation. In this model it was suggested that the T-helper cell, when recognising its antigen on a professional APC, would deliver an activation signal to the APC that as a result would be able to subsequently activate a CTL without the need for the T-helper cell to be present. Recently, the molecular mechanism of the licensing model was elucidated. Schoenberger et al. (Nature 393:480 (1998)), described the crucial role of the CD40L-CD40 pathway in the licensing model. Activation of the T-helper cell by the dendritic cell (DC) results in the up-regulation of the CD40L, which subsequently provides the signal that empowers the DC for CTL priming by triggering the CD40 molecule on the DC.

DC circulate through and are resident in the body tissues and at sites of antigen deposition or introduction. After taking up antigens, they migrate to the draining lymph nodes where they present antigen to the T cells. It is well known that a DC needs to be activated to perform optimally. Resting DC express only low levels of MHC and co-stimulatory molecules and are poor stimulators of T cells. DC can be activated by inflammatory cytokines and bacterial products, which results in up-regulation of MHC and co-stimulatory molecules. Therefore, DC that have encountered antigens under inflammatory conditions will readily activate T-helper cells when they arrive in the draining lymph nodes. It is thus very likely that the combination of inflammatory cytokines at the site of antigen uptake and the CD40L-CD40 interaction during the T-helper cell interaction result in an optimal capacity to license the DC for CTL activation.

The CD40 Molecule and the TNF Receptor Family

The CD40 molecule belongs to the TNF receptor family of type I transmembrane proteins. The members of this gene family (which include among others, the two receptors for TNF, the low-affinity nerve growth factor receptor and the T cell activation antigen CD27, CD30, and CD95) are characterized by sequence homology in their cysteine-rich extracellular domains (Armitage et al., Current Opinion in Immunology 6:407 (1994)). The known ligands for the members of the TNF receptor family are homologous as well. Although TNF-α is a soluble cytokine, it is initially synthesized as a membrane associated molecule. Most of the members of the TNF/CD40L receptor and the TNF/CD40 families are type 11 trans-membrane proteins. These include: hTNF-α, hLT, hLT-β, hCD40L, hCD27L, hCD30L, cfECP1, myx VRh, mCD30, hCD27, hFas, m4-1BB, rOX-40, hTNFR-h, hTNFR-II, hTNFP-1 and hLNGFR. CD40 is best known for its function in B-cell activation. The molecule is constitutively expressed on all B cells. CD40L-CD40 interaction can stimulate the proliferation of purified B cells and, in combination with cytokines, mediate immunoglobulin production. Recent studies indicate that the distribution of the CD40 molecule is not as restricted as was originally postulated. Freshly isolated human monocytes express low levels of the CD40 molecule, which can be upregulated by culturing them in the presence of IFN-α (Alderson et al., J. Exp. Med. 178:669 (1993)). Stimulation of monocytes via CD40 results in the secretion of pro-inflammatory cytokines such as IL-1 and TNF-α, toxic free radical intermediates such as nitric oxide and up-regulation of the B7 co-stimulatory molecules. Human DC isolated from peripheral blood can also express the CD40 molecule (Caux et al., J. Exp. Med. 180:263 (1994)). Ligation of CD40 on DC results in enhanced survival of these cells when cultured in vitro. As with monocytes, stimulation of DC via CD40 results in secretion of pro-inflammatory cytokines such as IL-12 and TNF-α and up-regulation of the CD80/86 co-stimulatory molecules. In addition, it was recently demonstrated that activation of CD40 induces the capacity to stimulate the activation of killer T cells (Schoenberger et al., Nature 393:480 (1998)). Accordingly, activating CD40 by binding it with a ligand, such as an antibody, would induce a number of humoral and cytotoxic effects, useful in inhibiting tumors.

SUMMARY OF THE INVENTION

The invention includes molecules able to bind to and activate CD40 expressed on both professional and non-professional APCs. These agonistic molecules, following binding to a cell surface receptor, induce intracellular signal transduction, leading to the activation of the APCs expressing CD40. The molecules of the invention include monoclonal antibodies, fragments thereof, peptides, oligonucleotides, and other chemical entities. Also included are peptides and genes inducing expression of anti-CD40 antibodies.

Such molecules can be used in combination, or in a bispecific or multivalent form, including as bispecific antibodies, to cross-link CD40 on the same cell, or to cross-link CD40 present on different cells. Either such cross-linking could cause a synergistic or additive agonistic effect.

The invention also provides a gene construct coding for an anti-CD40 monoclonal antibody or a fragment of an anti- CD40 monoclonal antibody. In this embodiment, the anti-CD40 antibody is produced by a hybridoma selected from the group consisting of hybridomas deposited with American Type Culture Collection (ATCC) as deposit designation PTA-2993, PTA-2994, PTA-2995, PTA-2996, PTA-2997, PTA-2998 and PTA-2999.

The present invention also provides a cell transfected with a gen construct coding fro the anti-CD40 monoclonal antibody.

BRIEF DESCRIPTION OF THE DRAWINGS

In the figures and as described below, anti-CD40 antibodies produced by hybridoma clones generated by the methods of the invention are referred to as follows, in relation to the hybridomas deposited with the American Type Culture Collection (ATCC) and given the following ATCC deposit accession numbers: clone 4 (hybridoma MAb 186-4-1, ATTC Accession No. PTA-2996), clone 7 (hybridoma MAb 186-7-2, ATCC Accession No. PTA-2997), clone 15 (hybridoma MAb 186-15-1, ATCC Accession No. PTA-2998), clone 21 (hybridoma MAb 186-21-1, ATCC Accession No. PTA-2993), clone 26 (hybridoma MAb 186-26-3, ATCC Accession No. PTA-2999), clone 64 (hybridoma MAb 186-64-1, ATCC Accession No. PTA-2994), clone 70 (hybridoma MAb 186-30-3, ATCC Accession No. PTA-2995). The hybridomas producing these antibodies were deposited with the ATCC (10801 University Blvd., Manassas, Va. 20110-2209, USA) in accordance with the provisions of the Budapest Treaty, on Jan. 31, 2001.

Applicants hereby state that all restrictions imposed by the depositor on the availability to the public of the deposited material will be irrevocably removed upon the granting of a U.S. patent based upon this application.

FIG. 1 shows the induction of maturation of monocyte derived DC by anti-CD40 monoclonal antibodies. Monocyte derived immature dendritic cells were cultured for two days in the presence of anti-CD40 monoclonal antibodies or isotype matched control antibodies and then studied by FACS analysis for up-regulation of expression of CD80 and down-regulation of the mannose receptor. Shown are the combined results of several experiments with the percentage of cells expressing CD83 in FIG. 1a and the relative decrease in mean fluorescence intensity (MFI) of the mannose receptor expression in unstimulated cells (MFI arbitrary taken as a value of 100) compared to stimulated cells in FIG. 1b.

FIG. 2 shows induction of maturation of monocyte derived DC by anti-CD40 monoclonal antibodies (clones 7, 15, 21, 48, 64 and 70). Monocyte derived immature dendritic cells were cultured for two days in the presence of anti-CD40 monoclonal antibody or isotype matched control antibodies and then studied by FACS analysis for up-regulation of expression of CD80, CD83 and CD86 and down-regulation of expression of the mannose receptor. Data of one representative experiment are shown: the CD80 (FIG. 2a), CD86 (FIG. 2c) and mannose receptor (FIG. 2d) expression are indicated as mean fluorescence intensity, whereas CD83 is indicated as the percentage of cells expressing this marker for mature dendritic cells (FIG. 2b).

FIG. 5 shows CD40 agonist monoclonal antibodies prime DC with an enhanced ability to induce CD8+ T cell responses. Monocyte derived DC were either left un-stimulated, or pre-activated with CD40 agonist antibody with or without IFN-γ and subsequently co-cultured with purified autologous CD8+ T cells in the presence of a flu matrix peptide representing a dominant HLA-A2 restricted epitope recognized by CD8+ T cells. The induction of CD8+ T cell responses by CD40 activated DC was studied by analyzing both the expansion of flu peptide specific CD8+ T cells 9 (FIG. 5a) and the increase in CD8+ T cells that produce IFN-γ (FIG. 5b).

DETAILED DESCRIPTION OF THE INVENTION

The molecules described and claimed include monoclonal antibodies, fragments thereof, peptides and other chemical entities. Monoclonal antibodies can be made by the conventional method of immunization of a mammal, followed by isolation of the B cell producing the monoclonal antibodies of interest and fusion with a myeloma cell. The preferred monoclonal antibodies include chimeric antibodies, humanized antibodies, human antibodies, DeImmunized™ antibodies, single-chain antibodies and fragments, including Fab, F(ab')$_2$ Fv and other fragments which retain the antigen binding function of the parent antibody. Single chain antibodies ("ScFv") and the method of their construction are described in U.S. Pat. No. 4,946,778.

Chimeric antibodies are produced by recombinant processes well known in the art, and have an animal variable region and a human constant region. Humanized antibodies correspond more closely to the sequence of human antibodies than do chimeric antibodies. In a humanized antibody, only the complementarity determining regions (CDRs), which are responsible for antigen binding and specificity, are non-human derived and have an amino acid sequence corresponding to the non-human antibody, and substantially all of the remaining portions of the molecule (except, in some cases, small portions of the framework regions within the variable region) are human derived and have an amino acid sequence corresponding to a human antibody. See L. Riechmann et al., Nature; 332: 323-327 1988; U.S. Pat. No. 5,225,539 (Medical Research Council); U.S. Pat. Nos. 5,585,089; 5,693,761; 5,693,762 (Protein Design Labs, Inc.).

Human antibodies can be made by several different methods, including by use of human immunoglobulin expression libraries (Stratagene Corp., La Jolla, Calif.; Cambridge Antibody Technology Ltd., London, England) to produce fragments of human antibodies (VH, VL, Fv, Fd, Fab, or (Fab')$_2$), and use of these fragments to construct whole human antibodies by fusion of the appropriate portion thereto, using techniques similar to those for producing chimeric antibodies. Human antibodies can also be produced in transgenic mice with a human immunoglobulin genome. Such mice are available from Abgenix, Inc., Fremont, Calif., and Medarex, Inc., Annandale, N.J. In addition to connecting the heavy and light chain Fv regions to form a single chain peptide, Fab can be constructed and expressed by similar means (M. J. Evans et al., J. Immunol. Meth., 184:123-138 1995).

DeImmunized™ antibodies are antibodies in which the potential T cell epitopes have been eliminated, as described in International Patent Application PCT/GB98/01473. Therefore, immunogenicity in humans is expected to be eliminated or substantially reduced when they are applied in vivo.

All of the wholly and partially human antibodies described above are less immunogenic than wholly murine or non-human-derived antibodies, as are the fragments and single chain antibodies. All these molecules (or derivatives thereof) are therefore less likely to evoke an immune or allergic response. Consequently, they are better suited for in vivo administration in humans than wholly non-human antibodies, especially when repeated or long-term administration is necessary, as may be needed for treatment of psoriasis or other inflammatory skin conditions.

Bispecific antibodies can be used as cross-linking agents between CD40 of the same cell, or CD40 on two different cells. Such bispecific antibodies would have one specificity for each of two different epitopes on CD40. Bispecifics in which one specificity is a strong activator of binding of sCD40L to CD40, and one specificity is a partial or non-inhibitor of binding of sCD40L to CD40, could synergize the agonistic effect on cross-linking.

These antibodies and the method of making them are described in U.S. Pat. No. 5,534,254 (Creative Biomolecules, Inc.). Different embodiments of bispecific antibodies described in the patent include linking single chain Fv with peptide couplers, including Ser-Cys, $(Gly)_4$-Cys, $(His)_6$-$(Gly)_4$-Cys, chelating agents, and chemical or disulfide couplings including bismaleimidohexane and bismaleimidocaproyl.

Non-antibody molecules can be isolated or screened from compound libraries by conventional means. An automated system for generating and screening a compound library is described in U.S. Pat. Nos. 5,901,069 and 5,463,564. A more focused approach involves three-dimensional modeling of the binding site, and then making a family of molecules which fit the model. These are then screened for those with optimal binding characteristics.

Another approach is to generate recombinant peptide libraries, and then screen them for those which bind to the epitope of CD40 of interest. See, e.g., U.S. Pat. No. 5,723,322. This epitope is the same as that bound by the monoclonal antibodies described in the examples below. Molecules can, in fact, be generated or isolated with relative ease in accordance with techniques well known in the art once the epitope is known.

Another approach is to induce endogenous production of the desired anti-CD40 antibodies, by administering a peptide or an antibody which induces such production, or through gene therapy, where a gene encoding an appropriate anti-CD40 molecule or a fragment thereof is administered. The method of making and administering any of these molecules is well known in the art.

The molecules can be administered by any of a number of routes. In the case of peptides and antibodies, because they are subject to degradation in the gastro-intestinal tract, they would preferably be injected. Other compounds of the invention could also be injected. The injections could be intramuscular, intravenous or sub-cutaneous.

Non-peptide molecules of the invention could be administered orally, including by suspension, tablets and the like. Liquid formulations could be administered by inhalation of lyophilized or aeorosolized microcapsules. Suppositories could also be used.

Additional pharmaceutical vehicles could be used to control the duration of action of the molecules of the invention. They could be entrapped in microcapsules prepared by coacervation techniques or by interfacial polymerization (hydroxymethylcellullose or gelatin microcapsules) in colloidal drug delivery systems (for example, liposomes, albumin microspheres, micro-emulsions, nanoparticles and nanocapsules) or in macro-emulsions.

Excipients, for example, salts, various bulking agents, additional buffering agents, chelating agents, antioxidants, cosolvents and the like can be included in the final formulation. Specific examples include tris(hydroxymethyl) aminomethane salts ("Tris buffer") and disodium edetate.

The dosage and scheduling for the formulation which is selected can be determined by standard procedures, well known in the art. Such procedures involve extrapolating an estimated dosing schedule from animal models, and then determining the optimal dosage in a human clinical dose ranging study.

Examples of molecules of the invention are set forth below.
Making and Using Agonistic Monoclonal Antibodies
A. Materials and Methods
In the Examples set forth below, the following procedures were used, as indicated in the examples.

Cell Lines and Culture Conditions

The EBV-transformed B-cell line JY and the myeloid derived cell line THP1 were cultured in T75 culture flasks routinely in Iscove's modified Dulbecco's medium (IMDM) to which 50 .quadrature.g/ml gentamycin and 2% heat inactivated foetal calf serum was added (FCSi; BioWhittaker, Verviers, Belgium). The cells were cultured in a humidified incubator at 37° C. and 5% $CO_2$ Once or twice per week the cells were split ({fraction (1/20)} to {fraction (1/100)}). To store the cell line, ampoules were made containing 5-10×10$^6$ cells/ml Hank's balanced salt solution HBSS supplemented with 20% FCSi and 10% DMSO, and stored in the liquid nitrogen.

Peripheral Mononuclear Blood Cell Isolation and Storage

Peripheral mononuclear blood cells (PBMC) were isolated from "buffy coats" of healthy donors by Lymphoprep™ (1.077 g/ml) density centrifugation and resuspended in $Ca^{2+}$/$Mg^{2+}$-free PBS-0.1% BSA. Autologous PBMC were stored in RPMI 1640 supplemented with 2 mM L-glutamine, 10% FCSi, 50 μg/ml gentamycin and 10% DMSO at −196° C. (for CD8 T cell purification, see below).

Monocyte Enrichment and Generation of Monocyte-Derived Immature DC

Monocytes were purified from PBMC by immunomagnetic depletion (monocyte-enrichment cocktail containing Mabs against CD2, CD3, CD16, CD19, CD56, CD66b and glycophorin A; StemSep™ from StemCell Technologies, Vancouver, Canada). Monocyte (>90% CD14+) preparations devoid of neutrophilic granulocytes, platelets, lymphocytes and NK cells were subsequently cultured in serum-free culture medium, StemSpan™ (StemCell Technologies), supplemented with 10 ng/ml GM-CSF and 20 ng/ml IL-4 (both cytokines from PeproTech, Rocky Hill, N.J., USA) at 37° C./5% $CO_2$ during 6-7 days. These monocytes were seeded at a cell density of 1×10$^{6/2}$ ml/10 cm$^2$ polystyrene surface (coated with 12 mg/ml/10 cm$^2$ poly-hydroxethylmethacrylate; Sigma) and fresh GM-CSF/IL-4 was added at day 2 and 5. After 6-7 days, the nonadherent cells (with a dendritic morphology) were collected and displayed the following (flow cytometry, see below) phenotypic profile: $CD1a^+$, $CD14^-$, $CD40^+$, $C80^+$, $CD83^-$, $CD86^+$, $HLA-DR^+$ and mannose receptor$^{++}$.

CD8 T Lymphocyte Isolation

Autologous PBMC were thawed, and CD8 T lymphocytes were purified by immunomagnetic depletion of other cell types (CD8-enrichment cocktail with Mabs against CD4, CD14, CD16, CD56 and glycophorin A; StemCell Technologies). This procedure resulted in >90% CD3+/CD8+ lymphocytes devoid of monocytes, neutrophilic granulocytes, platelets, B and CD4 lymphocytes, and NK cells.

Flow Cytometric Analyses

Cells ($0.1 \times 10^6$ cells/100 µl PBS-0.1% BSA/sample) were incubated with conjugated (to either fluorescein isothiocyanate, phycoerythrin or peridinin chlorophyll protein) Mabs (Becton & Dickinson, Woerden, The Netherlands) for 15 min. at 21° C., and then thoroughly washed in PBS-0.1% BSA and analyzed on a flow cytometer (FACSCalibur™; Becton & Dickinson, Woerden, The Netherlands).

Competition of CD40 Ligand and Anti-CD40 Monoclonal Antibodies on JY Cells

Blocking of soluble CD40 ligand (sCD40L) binding by anti-CD40 monoclonal antibodies (Mabs) was demonstrated by using JY cells, which express high levels of CD40. These cells ($0.1 \times 10^6$ cells/100 ml PBS-0.1% BSA/sample) were pre-incubated with anti-CD40 Mabs for 15 min. at 21° C., and then thoroughly washed in PBS-0.1% BSA, followed by an incubation with a soluble fusion protein consisting of the extracellular domain of human CD40L fused to the extracellular domain of murine CD8α (CD40L-mCD8a; Kordia, Leiden, The Netherlands and Tanox Pharma BV, Amsterdam, The Netherlands) for 15 min. at 21° C. Subsequently, CD40L-mCD8a was detected by using rat anti-mouse CD8α coupled to phycoerythrin, and analyzed by flow cytometry.

Well-characterized control Mabs were included as controls: M2 and G28-5 compete for the CD40L binding site, and 5C3 binds to a region distinct from the CD40L binding site. EA-5 partially inhibits the binding of CD40L to its receptor (Pound et al., Int Immunol 1999, 11, p 11-20).

Inhibition of Binding of Anti-CD40 Monoclonal Antibodies to Membrane CD40L by CD40-Fc (IgG4).

As a source of membrane CD40L activated CD4+ T cells are used. To this purpose expression of CD40L on T cells is induced through culturing plastic non-adherent PBMC with PMA and ionomycine for 6 hrs in IMDM+5% human pooled AB serum. CD40-Fc (IgG4 made by Tanox Inc Houston USA) is directly added at a saturating dose to the activated T cells or after pre-incubation of CD40Fc with excess of anti-CD40 Mabs. Binding of CD40-Fc to CD40L activated CD4+ (CD3+CD8−) T cells is monitored through FACS analysis after staining with PE conjugated goat anti human IgG-Fc, FITC conjugated CD3 and PERCP conjugated CD8.

CD40 ELISA

ELISA plates (Immunon 2) were coated overnight at room temperature with 0.5 µg/ml, 50 µl per well of goat-anti-human IgG (Fc). Next the plates were treated with 1% BLOTTO for 60 min at room temperature. After washing 4 times with PBS/Tween, 50 µl/well of CD40Fc plus 50 µl of supernatants of the fusion wells were added and incubated for 1 hour at room temperature. After another 4 washings with PBS/Tween, 50 µl of goat-anti-mouse IgG (Fc)-HRP conjugate was added and incubated for 1 hour. After 4 washings the substrate TMB was added at 100 µl/well to the plates which were incubated for 30 min. The reaction was stopped by addition of 50 µl/well of 0.2 M $H_2SO_4$ and the plates were read with an ELISA reader at 450/590 nm THP-1 assay Stimulation of THP-1 Cells $3 \times 10^6$ THP-1 cells were first cultured for two days in 10 ml of IMDM+2% of human type AB serum in the presence of $5 \times 10^2$ U/ml IFN-.quadrature. Next the IFN-g treated THP-1 cells were washed once in IMDM+2% human type AB serum. $10^4$ THP-1 cells per 96 w plate well were cultured for two days in 120 µl of culture medium diluted 1:2 with hybridoma supernatant. As controls CD154-mCD8 was used at 40 .quadrature.g/ml maximum and 2× dilutions and LPS at 20 ng/ml maximum and 2× dilutions.

Measurement of IL-8

ELISA plates were coated with mouse anti human IL-8 antibody (Serotec) at 5 µg/ml, 100 .quadrature.l/well for 2 hrs at room temperature on a plate shaker. The plates were then incubated with 1% BLOTTO for one hour on the plate shaker at room temperature. After four washings with PBS/Tween, 80 µl of supernatants harvested from the THP-1 plate were added to the ELISA plate. For the IL-8 standards: IL-8 was diluted with 1% BLOTTO to 1000 pg/ml, 300 pg/ml, 100 g/ml 30 pg/ml, 10 pg/ml, 3 pg/ml, 1 pg/ml. The ELISA plates were incubated for one hr at room temperature on the plate shaker. After four washings with PBS/Tween, 100 µl/well mouse-anti IL-8 biotin conjugate (Serotec) was added at 1:1000 dilution in 1% BLOTTO and the plates were incubated for one hour at room temperature. After four washings with PBS/Tween, 100 .quadrature.l/well AMDX SA-HRP at 1:1000 dilution in 1% BLOTTO was added to the wells and the plates were incubated for 1 hour at room temperature on the plate shaker. After 4 washings with PBS/Tween, 100 .quadrature.l of TMB substrate was added to each well and the plates were incubated for 30 minutes at room temperature on the plate shaker. The reaction was stopped by addition of 50 µl/well of 0.2 M $H_2SO_4$ and the plates were read with an ELISA reader at 450/590 nm.

Induction of Mature DC

Immature DC (see above) are cultured in the presence of anti-CD40 Mabs under serum-free condition (StemSpan™) at 37° C./5% CO2 for 48 hours. In addition, CD40L-mCD8u, LPS and a combination of IL-1β and TNF-β are used as well-established controls for DC maturation. The change from immature to mature DC is determined by: (1) phenotype (CD1a+, CD14−, CD40+++, CD80+++, CD83+, CD86+++, HLA-DR+++, mannose receptors), (2) IL-12p70 production (commercially available kit), and by (3) the capability of inducing influenza-matrix peptide specific autologous cytotoxic CD8+++T lymphocytes (see below).

IL-12p70 ELISA

Immature DC are cultured in the presence of anti-CD40 Mabs (1 µg/ml) with or without IFN-g (1000 U/ml) for 48 hrs. IL-12p70 secretion was measured in the supernatant using a commercially available kit from Diaclone Research, Becanson, France. Inhibition of IL-12 production was obtained by preincubation of anti-CD40 Mabs with 10 times excess of CD40-Fc (IgG4 made by Tanox Inc Houston USA) for 15 min at room temperature.

Induction of Cytotoxic CD8+ T Lymphocytes By Mature DC

Mature DC generated by agonistic anti-CD40 Mabs are loaded with a synthetic influenza matrix peptide (Flu-peptide 58-66); $1 \times 10^6$ DC/Flu-peptide 5 µg/ml StemSpan™) and co-cultured with $0.5 \times 10^6$ purified autologous CD8+ T lymphocytes at 37° C./5% $CO_2$ during 7 days. Cytotoxicity of the CD8+ T lymphocytes is determined by: (1) enumeration of the number of IFN-γ producing T cells, which are representative for activated CTL (using flow cytometry with an IFN-γ detection kit from Miltenyi Biotec, Bergisch Gladbach, Germany), and (2) a convential assay measuring cytolysis by CTL of target cells loaded with Flu-peptide.

EXAMPLES

Example 1

Generation of Mouse Anti-Human CD40 Monoclonal Antibodies

Two immunization protocols were used to generate anti-CD40 monoclonal antibodies. In the first, female BALB/c mice were injected intraperitoneally with SF-9 cells expressing CD40 ($3 \times 10^6$ cells/mouse), which were washed with PBS twice before injection. At day 17 and 31 the mice received a booster injection with SF-9 cells. Fourteen days after the last the last the injection the spleen cells were isolated and $10^8$ cells were used for cell fusion with $10^8$ SP2/0 murine myeloma cells using polyethylene glycol. The fused cells were resuspended in D15 (a modified DMEM medium) supplemented with HAT, followed by plating on fifty-one 96 wells plates. After 10-14 days supernatants of wells containing growing hybridoma cells were screened for anti-CD40 antibody production in an ELISA. This analysis showed that a total of 69 wells out of 4896 seeded wells contained hybridomas producing anti-human CD40 specific antibodies. Culture supernatants of these wells were selected for additional experiments, such as for studying the induction of IL-8 secretion from THP-1 cells (see below). Next limiting dilution was performed twice to obtain clones from a number of hybridoma lines that produced CD40 agonist antibodies. For this purpose hybridoma cells were seeded at densities of less than 1 c/well in 96 well plates and cultured for 3-4 weeks. Supernatant of positive wells was screened in the CD40 ELISA and the THP-1 assay for the presence of CD40 binding antibodies.

For the second immunization regimen, BALB/c mice were injected intraperitoneally with $2.5 \times 10^6$ monocyte-derived immature DC. At days 14, 35 and 55 mice received booster injections with monocyte-derived DC from different donors. At around day 100-120, spleen cells will be isolated and fused with murine myeloma cells in analogy to the above protocol. Supernatants of wells with growing hybridomas will be screened for the presence of CD40 binding antibodies in the ELISA. Hybridoma supernatants containing CD40 binding antibodies will be subsequently screened for potential agonistic activity as described for the hybridoma's originating from B cells isolated from the BALB/c immunized with CD40 expressing SF-9 cells

Example 2

Screening the Cd40 Binding Antibody Samples from Hybridoma Lines for Agonistic Activity on THP-1 Cells and Subsequent Cloning of Lines and Testing of Monoclonal Mabs To screen for antibodies with agonistic activity, the selected supernatants containing CD40 binding antibodies were subsequently tested for their ability to induce IL-8 production in the CD40 expressing monocytic cell line THP-1, which had been pre-incubated with IFN-γ. As shown in table 1, most supernatants contained anti-CD40 antibodies, which displayed agonistic activity in this assay. Supernatants were arbitrarily subdivided into four different groups on the basis of their performance in the THP-1 assay (strong agonists with an OD of >2.000, intermediate agonists with an OD between 1.000-2.000, low agonists with an OD between 0.375-0.999 and non-agonists with an OD<0.375).

A number of the hybridoma lines were cloned and monoclonal antibodies from the resulting clones were also tested in the THP-1 assay. Most but not all clones retained the reactivity pattern of the corresponding mother lines (data not shown).

Example 3

Figure 1A:
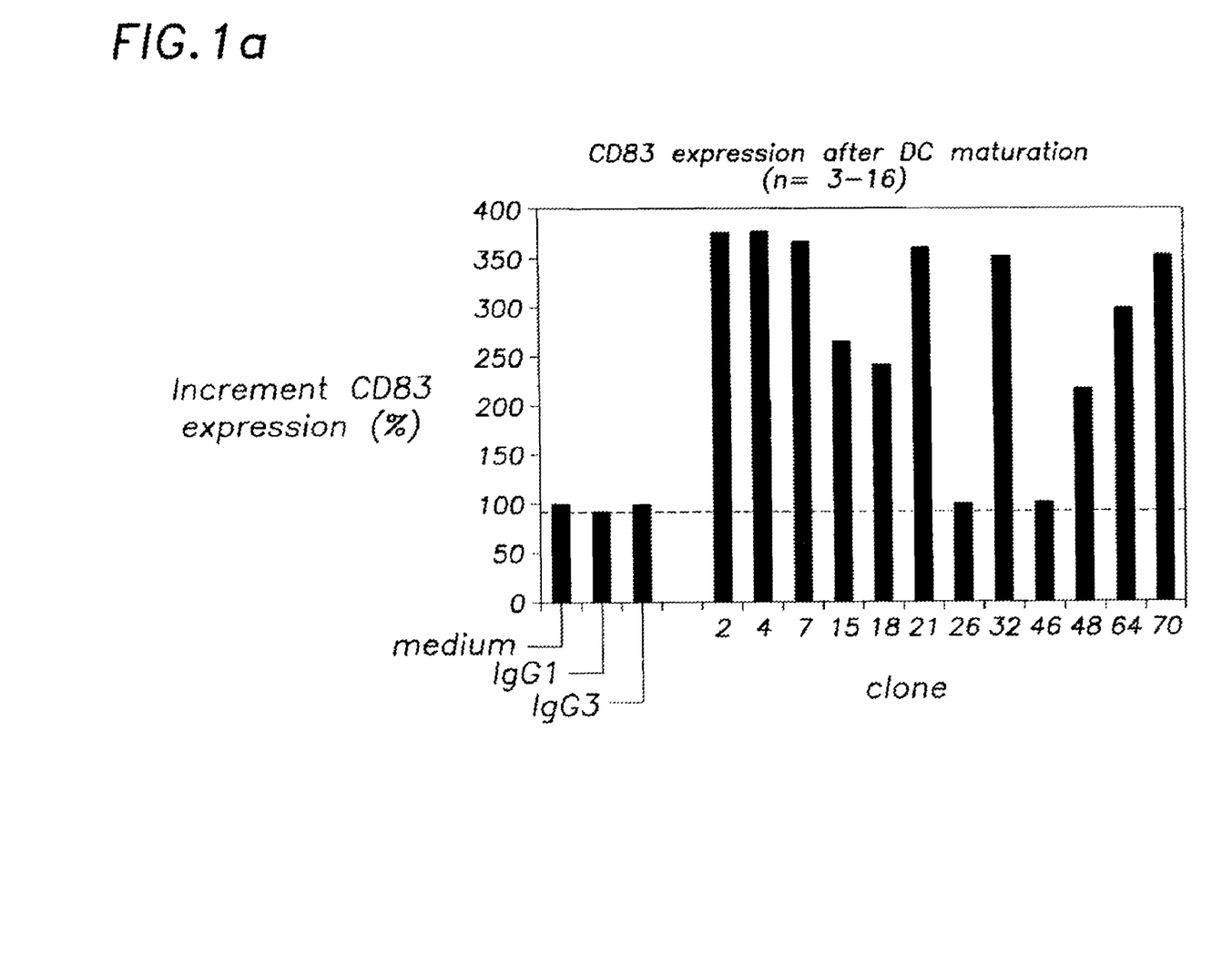
Figure 1B:
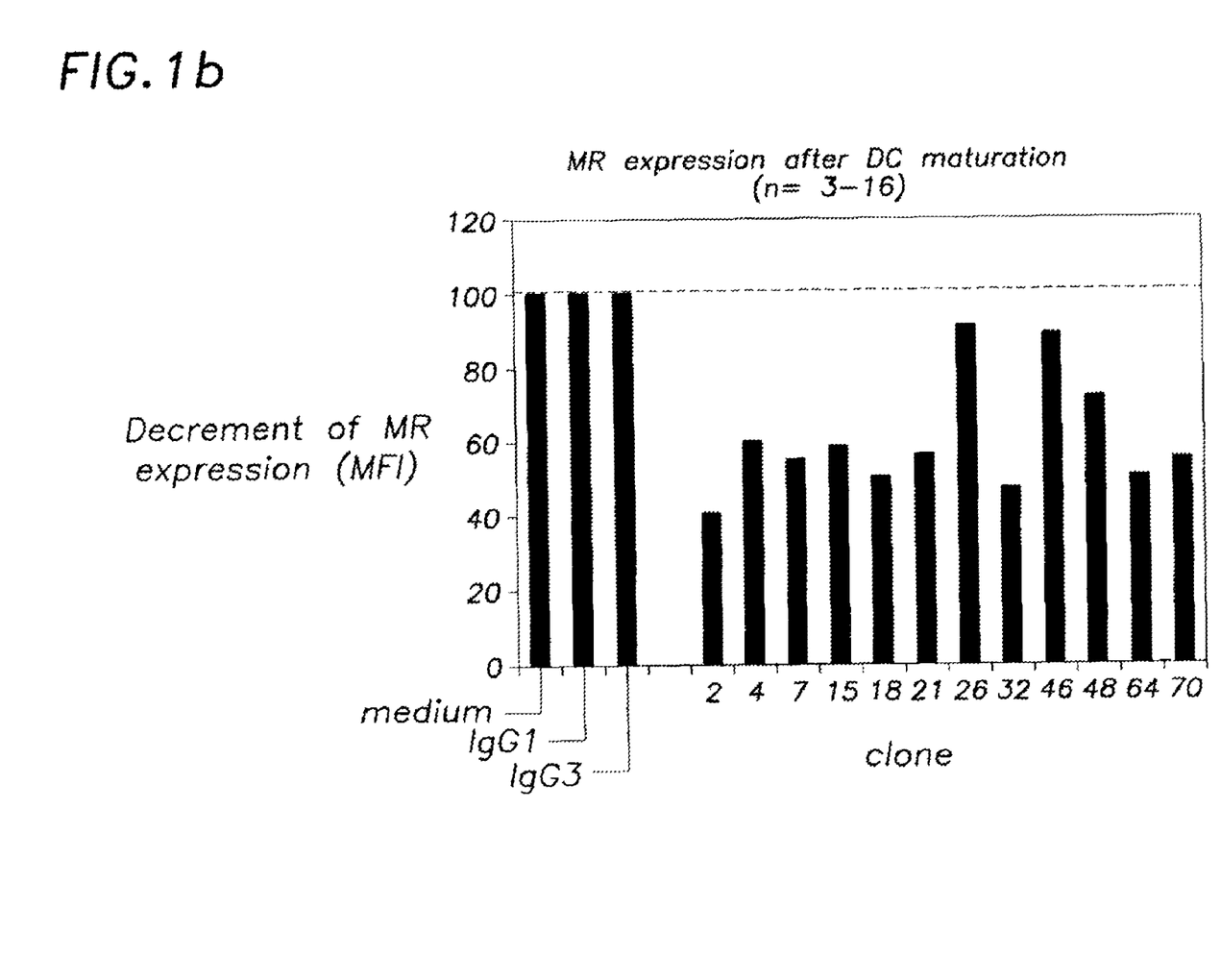
Figure 2A:
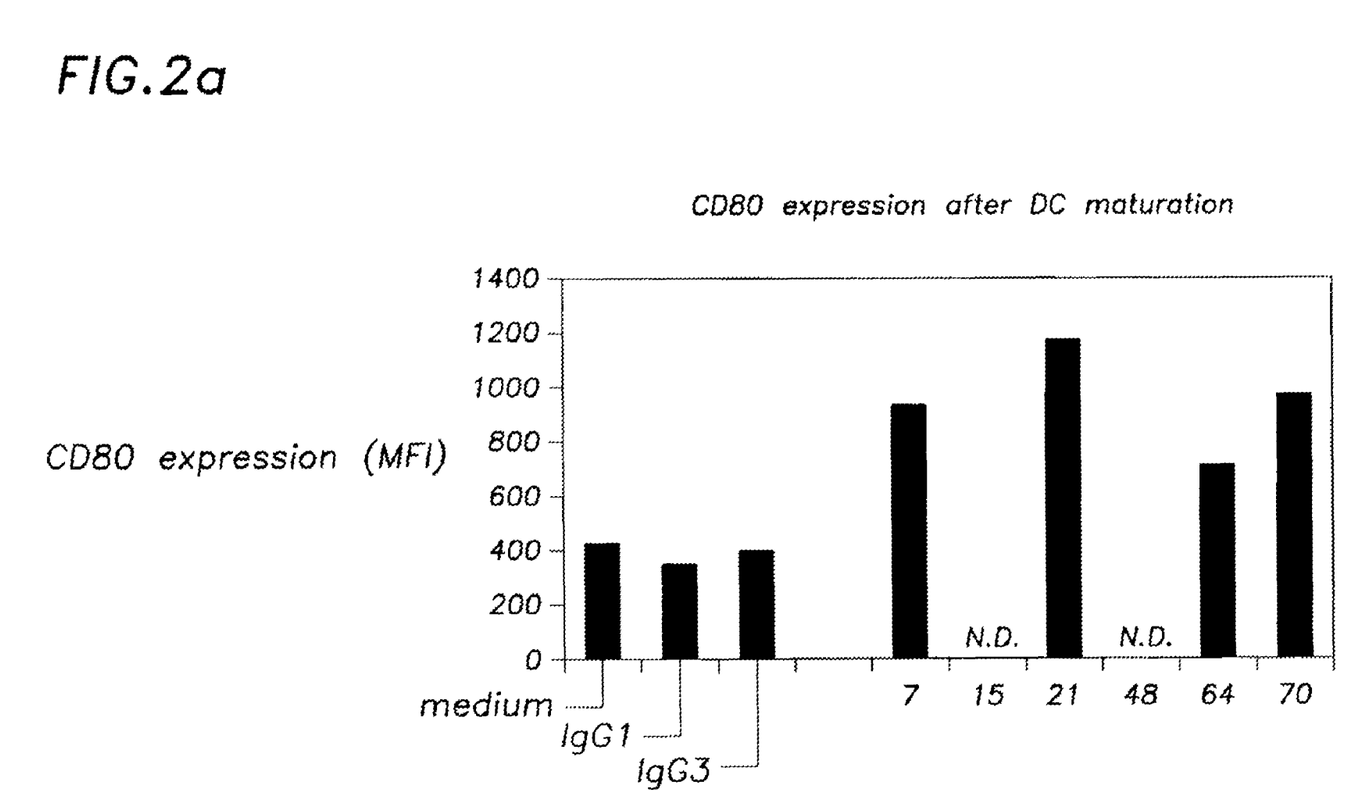
Figure 2B:
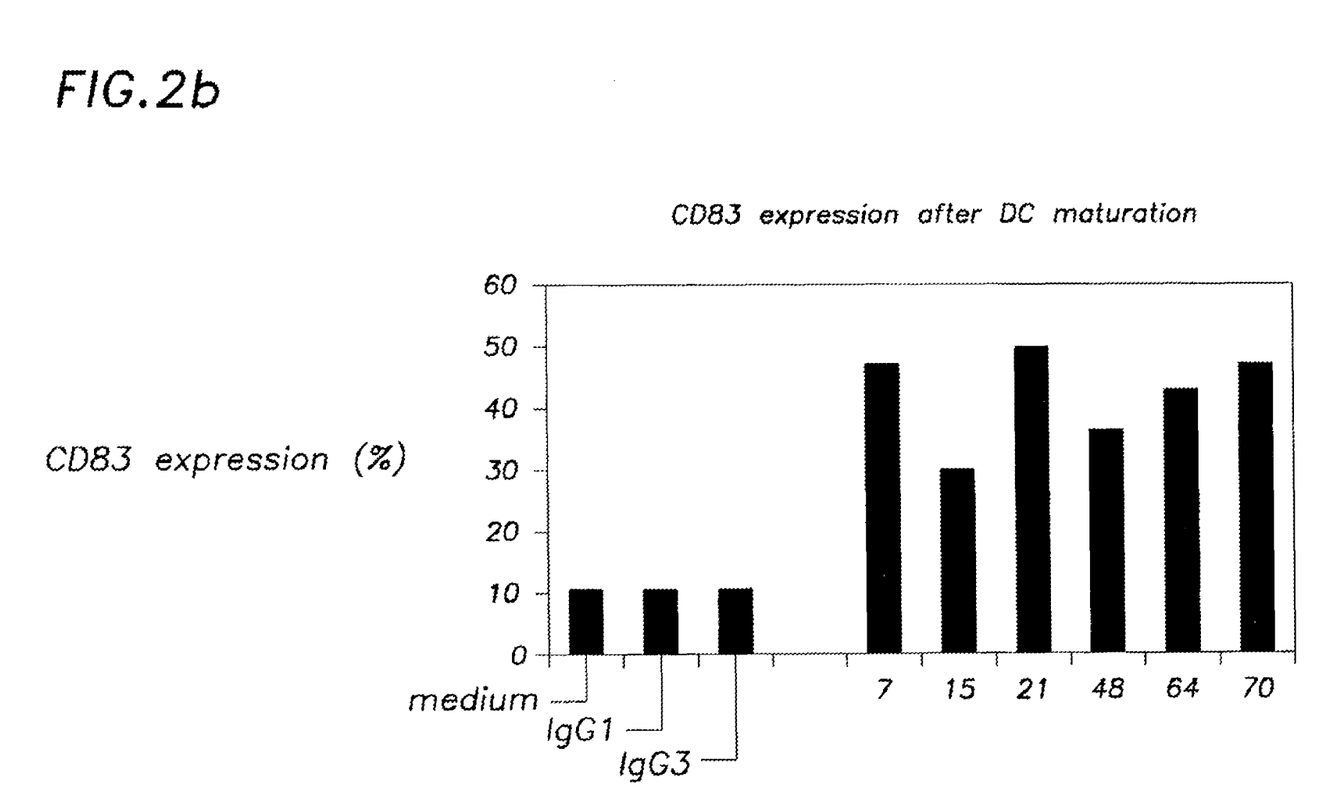
Figure 2C:
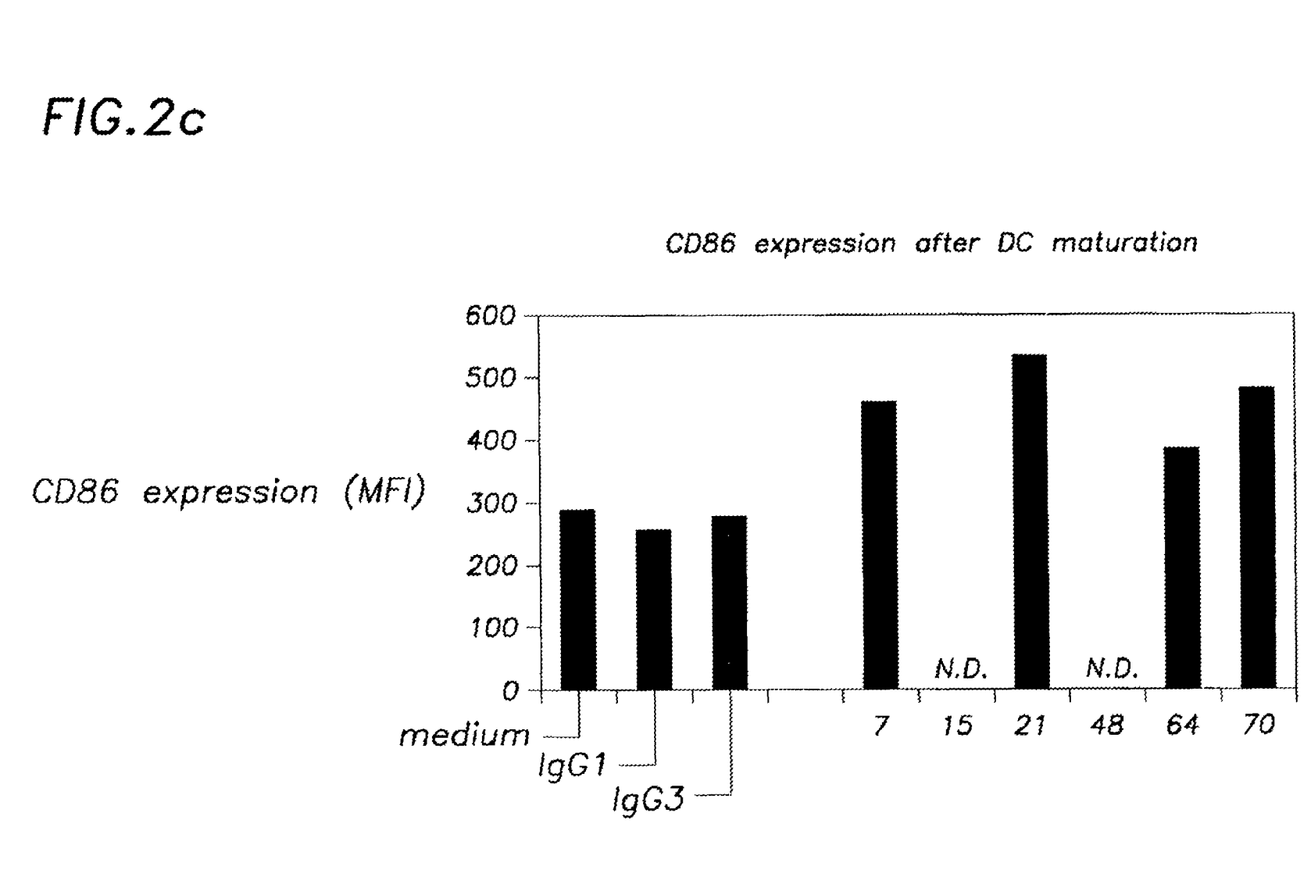
Figure 2D:
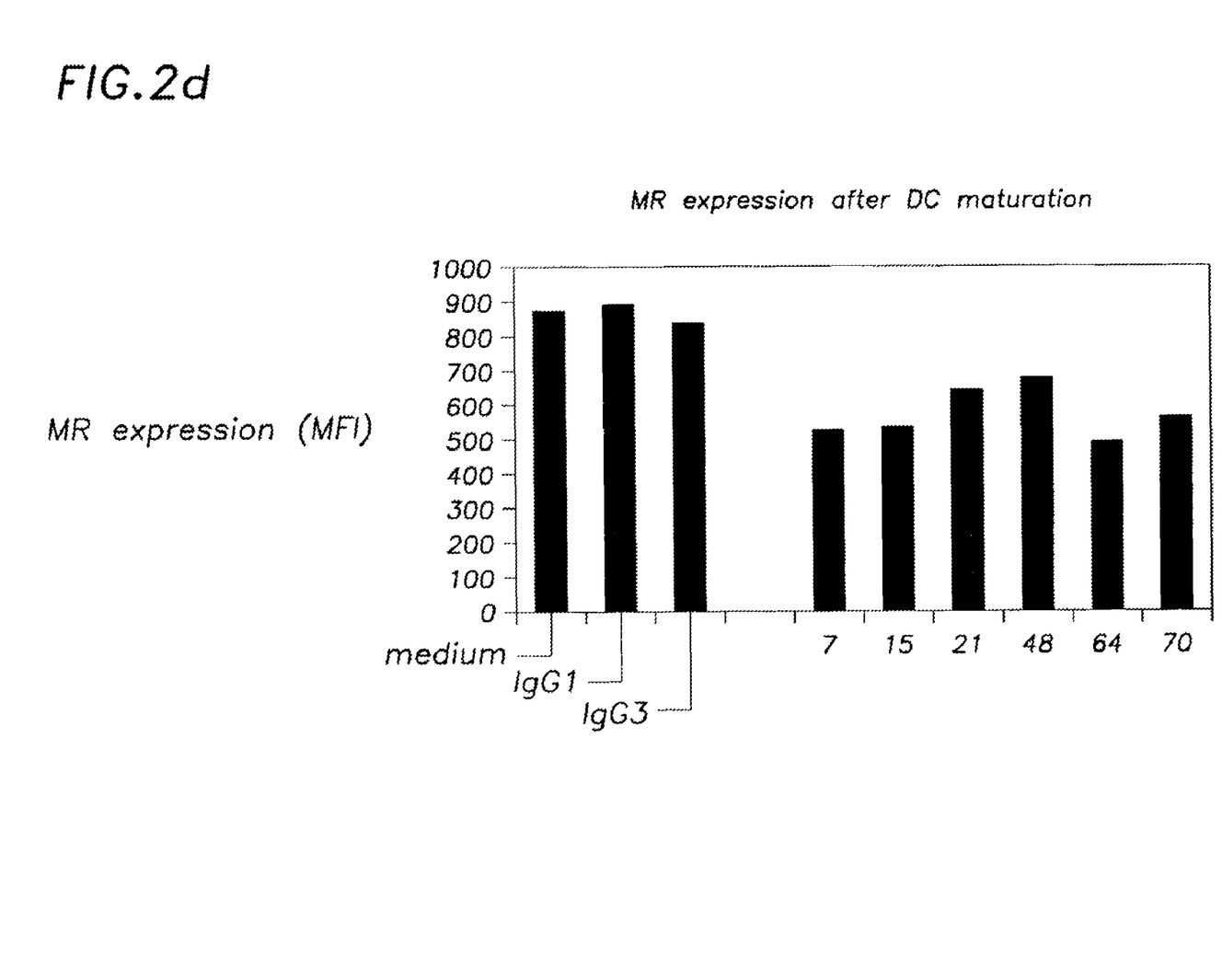

Assaying the Ability of the CD40 Reactive Antibody Clones to Drive Maturation, IL-12p70 Production and Priming for CTL Activation of Immature DC DC derived from monocytes after culture with GM-CSF and IL-4 represent immature DC. Anti-CD40 monoclonal antibodies have been assayed for their capacity to induce maturation of these CD40 expressing immature DC. Experiments from other investigators have shown that stimulation of monocyte-derived DC with sCD40L results in their differentiation into DC with a mature phenotype. Furthermore, sCD40L in combination with IFN-γ stimulates monocyte-derived DC to secrete IL-12p70. In contrast to immature DC, mature DC express CD83. In addition, compared to immature DC, mature DC display enhanced expression on a per cell basis of the co-stimulatory molecules CD80 and CD86, decreased expression of the mannose receptor and loss of the ability to efficiently take up molecules, as shown for dextran-FITC. At first the phenotypical changes that accompany the differentiation of immature to mature DC were monitored by FACS-analysis as a read-out for induction of DC maturation by the anti-CD40 monoclonal antibodies. Antibodies were first used on their own to stimulate monocyte-derived DC. As shown in FIG. 1 (combined results of several experiments showing CD83 up-regulation and mannose receptor down-regulation) and in FIG. 2 (one typical experiment showing induced expression of CD80, CD83 and CD86) CD40 binding antibodies were tested and were found to induce phenotypical maturation of monocyte derived DC, as is indicated by the increased percentage of cells expressing the CD83 marker, the increased expression on a per cell basis (mean fluorescence intensity; MFI) of CD80 and CD86 and decreased expression of the mannose receptor. Remarkably, some of the clones that did not induce IL-8 production in THP-1 cells could induce maturation of DC, demonstrating that agonist properties of CD40 monoclonal antibodies may differ between different CD40 expressing cell types (data not shown).

Figure 3:
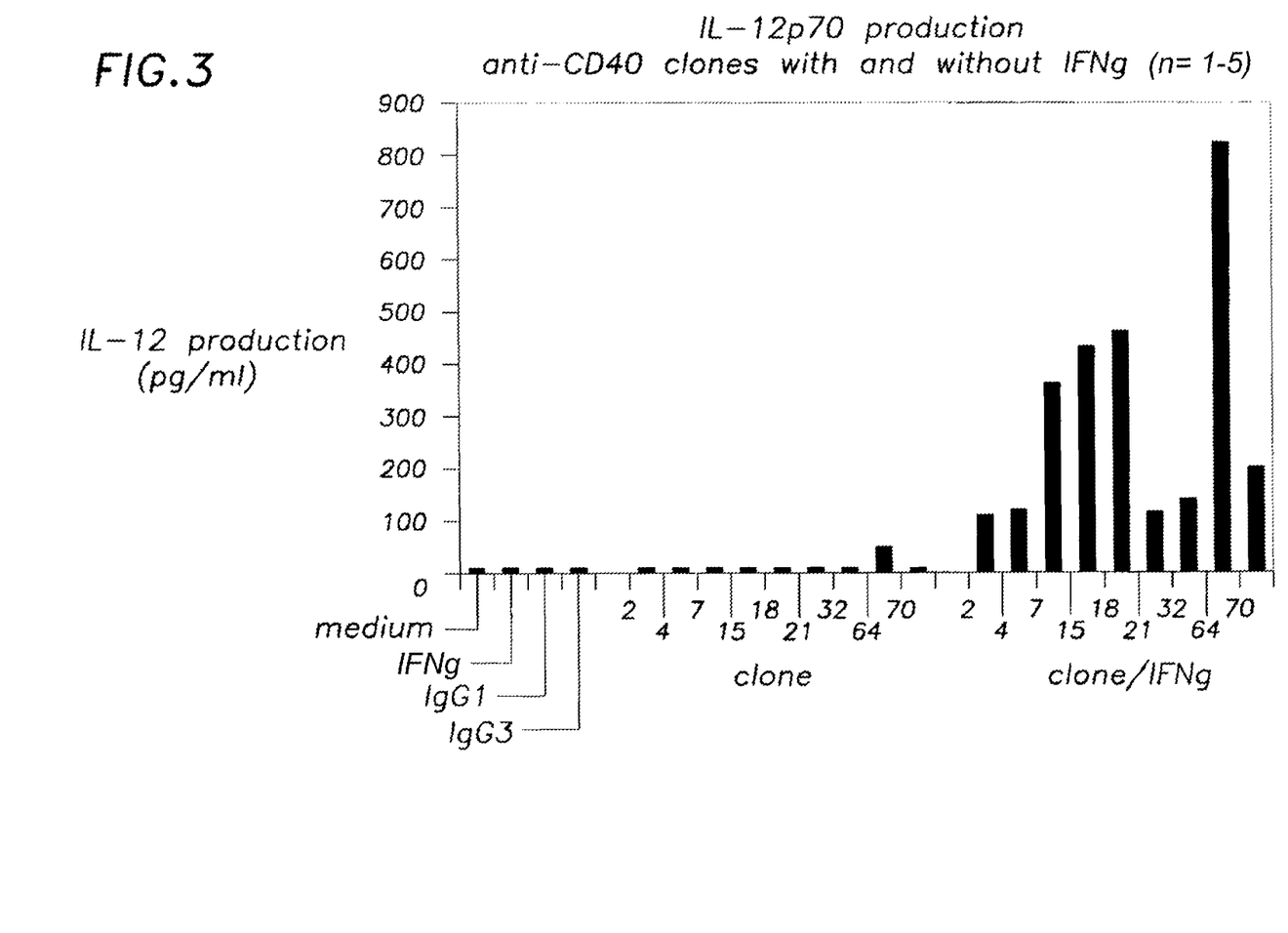
FIG. 3 shows induction of IL-12p70 secretion by monocyte derived DC after stimulation with CD40 agonist antibodies and IFN-γ. Monocyte derived immature DC were cultured for two days in the presence of anti-CD40 monoclonal antibodies or isotype control antibodies alone or in combination with IFN-γ. Induction of IL-12p70 production requires the combination of two different stimuli.
Figure 4:
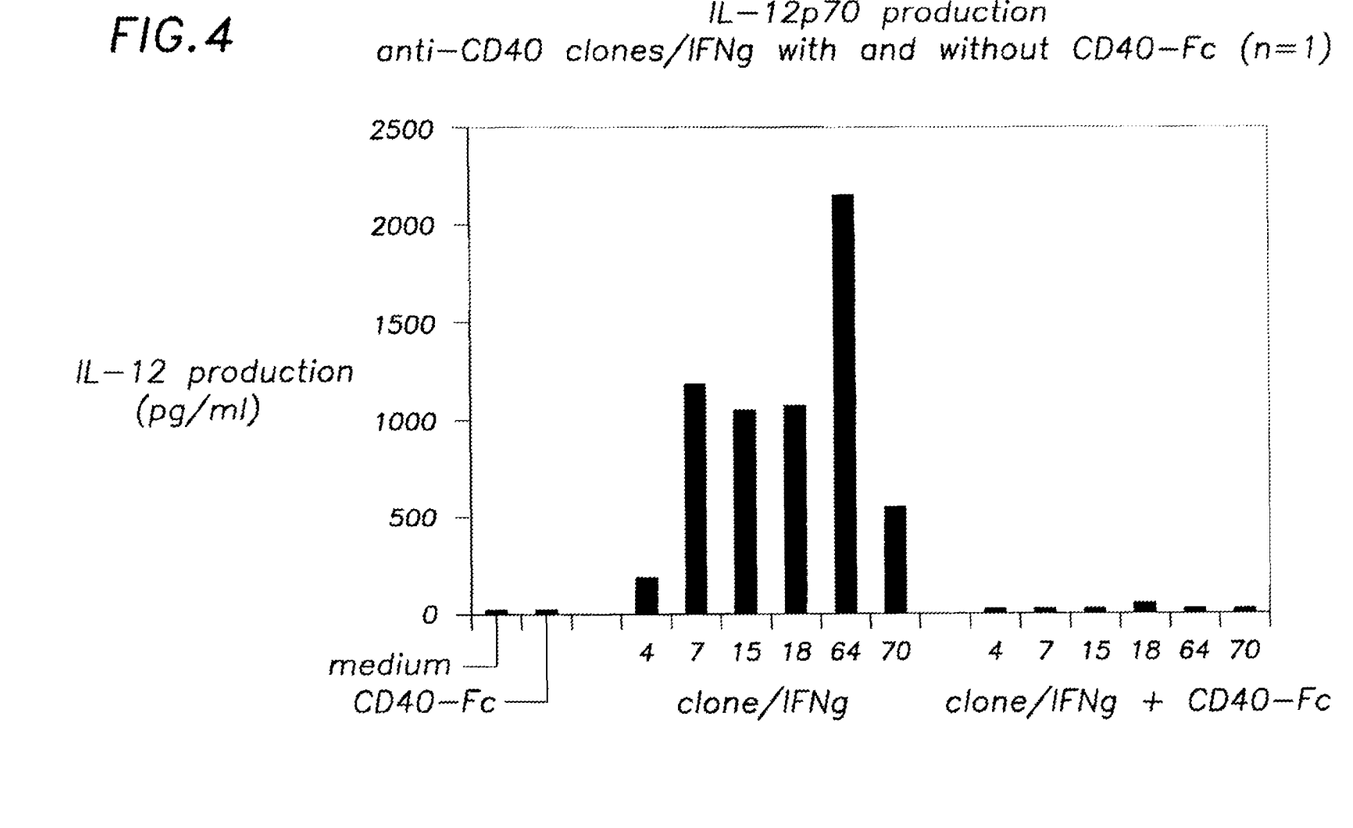
FIG. 4 shows IL-12p70 production induced by CD40 agonist antibodies and IFN-γ is blocked by pre-incubation with CD40-Fc. Pre-incubation of the CD40 agonist antibodies with an excess of CD40-Fc abolished the ability of the anti-CD40 monoclonal antibodies to induce, in combination with IFN-γ, IL-12 production in monocyte derived DC.

In addition, the IL-12p70 production of monocyte derived DC was tested after stimulation with the CD40 monoclonal antibodies and IFN-γ since dendritic cells require stimulation through at least two different pathways to produce IL-12p70 (Kalinski et al Blood 1997 90:1926). Our results show that apart from induction of phenotypical maturation, the CD40 agonist antibodies also induced IL-12 production in DC when used together with IFN-γ (FIG. 3). Our finding that pre-incubation of the CD40 monoclonal antibodies with excess of CD40-Fc inhibited induction of IL-12 production demonstrated that the agonistic effect of the antibodies is really exerted through CD40 and not through other membrane expressed molecules on the DC (FIG. 4).

In the mouse, T cell help to CTL was found to be mediated through CD40 activated DC. Antigen dependent interaction of helper T cells with DC did not only result in the activation of the helper T cell, but through CD40L-CD40 interaction also in the activation of the DC. Only in their activated stage DC were able to prime CTL responses. In the absence of helper T cells no DC activation and therefore no CTL priming occurred. However, by means of in vivo administration of an anti-mouse CD40 stimulatory antibody, T cell help could be efficiently bypassed and DC directly activated.

Figure 5A:
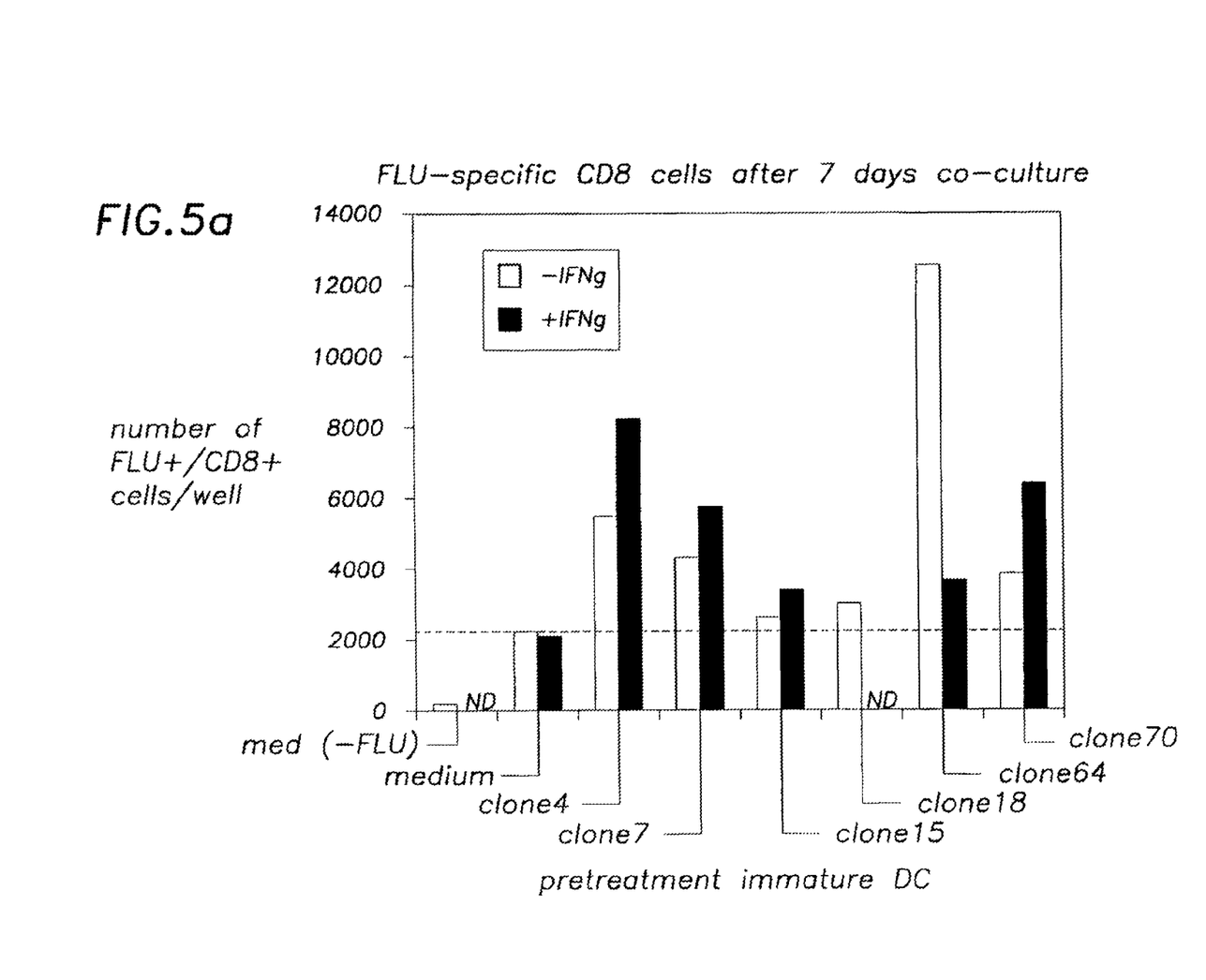
Figure 5B:
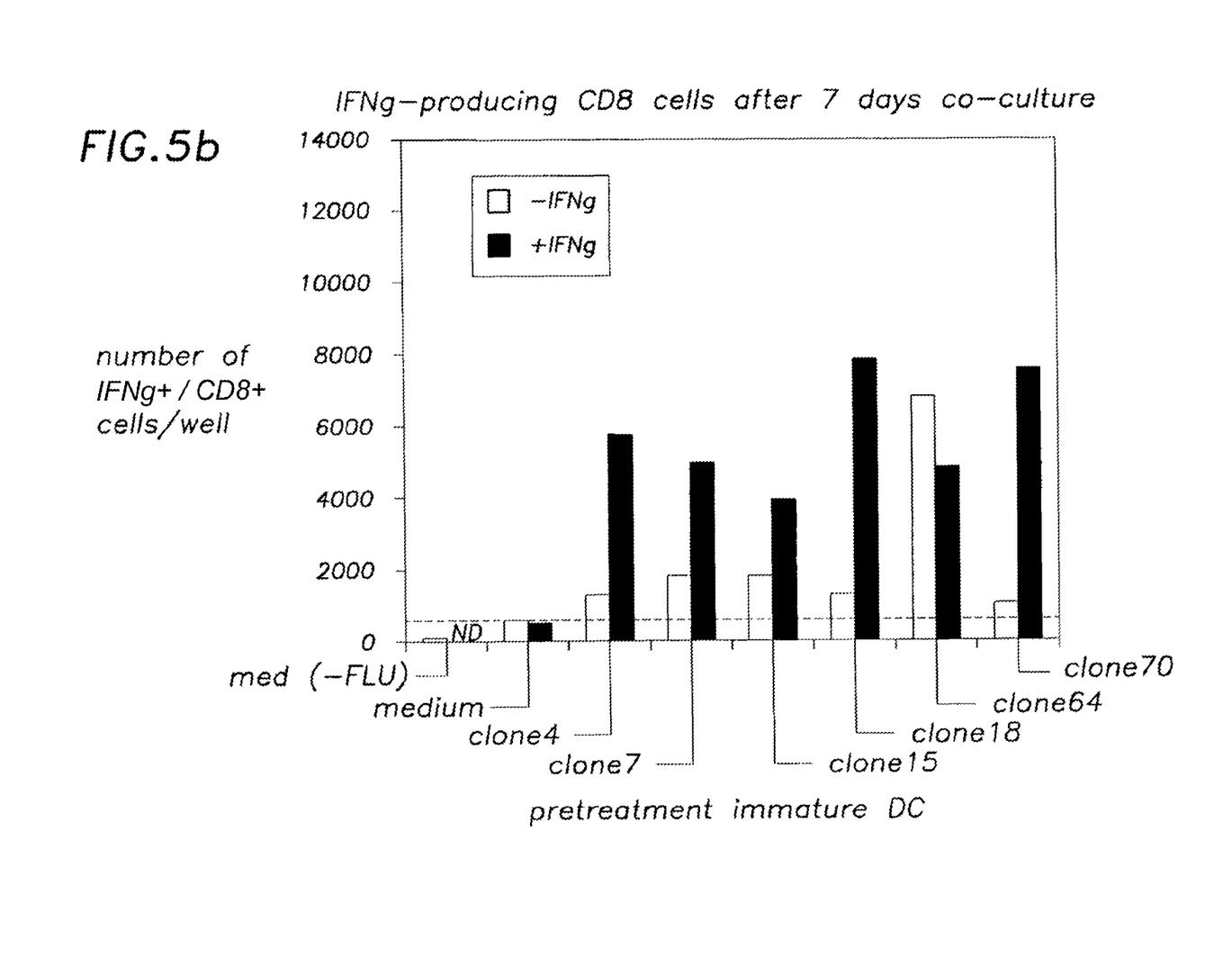

To show that the same mechanism of CTL activation applies to man, an in vitro study was performed in which CTL activation was studied in a co-culture system consisting of purified human CD8+T cells, monocyte-derived DC as APC and a minimal peptide derived from influenza virus matrix protein as antigen. This peptide constitutes a dominant HLA-A2 restricted CTL epitope. This experiment was carried out to establish whether our anti-CD40 monoclonal antibodies could empower monocyte-derived DC with an increased ability to stimulate CTL responses compared to untreated control DC. CTL activation was analyzed in this experiment through measurement of production of IFN-γ by activated CTL and enumeration of expansion of CTL with PE conjugated HLA-A2/influenza matrix peptide tetramers. As shown in FIG. 5a and b the stimulation of monocyte derived DC with CD40 monoclonal antibodies led to increased ability of these cells to induce a flu peptide directed CD8+ T cell response. For most antibodies this effect was elevated when, in addition to the monoclonal antibodies, IFN-γ was used in the pre-activation of the dendritic cells.

Example 4

Analysis of the Inhibition of the Binding of sCD40L to CD40 by the Anti-CD40 Antibody Samples Anti-CD40 antibodies that synergize with sCD40L in the induction of CD40 mediated activation of DC most likely show co-binding with sCD40L to CD40 and thus do not display strong blocking of binding of sCD40L to CD40. To screen for such antibodies, the percentage of inhibition of sCD40L binding to CD40 on JY EBV transformed B cells by the monoclonal antibodies was tested. This analysis revealed that there was strong variation in the degree that the monoclonal antibodies could inhibit the binding of sCD40L to CD40. Some antibody samples almost completely inhibited sCD40L binding, whereas other antibody samples could only partially block sCD40L binding or had no effect at all (table 2). The results were confirmed in the reverse way for a limited number of clones by testing the inhibition caused by the anti-CD40 monoclonal antibodies of the binding of CD40-Fc to CD40L expressed on the membrane of PMA+ionomycine activated CD4+ T cells. In this experiment clone 4 blocked binding of CD40-Fc to CD40L on the T cells for 88%, clone 7 and 64 for respectively 16% and 25%. Although there was no absolute correlation between the performance of the antibodies in the DC maturation and the THP-1 assay and their ability to block sCD40L binding to CD40, all the clones that did not block this interaction were non-responders in both assays (data not shown)

Example 5

Synergism Between Anti-CD40 Antibodies and mCD40L or sCD40L in Agonist Activity on DC It is predicted that those antibodies that to a major extent block binding of sCD40L to CD40 will not display synergism with sCD40L in the induction of DC maturation or other agonistic properties exerted on CD40 positive cells. In contrast, some of the CD40 binding antibodies that efficiently co-bind with sCD40L to its receptor will presumably show synergism with sCD40L or membrane bound CD40L (mCD40L) in driving DC maturation. (As a source of membrane bound CD40L antigen or mitogen activated CD4+ T cells will be used) This will be demonstrated by the increased percentage of cells expressing CD83, by the increased expression on a per cell basis of CD80 and CD86 and the decreased expression of the mannose receptor. Also the level of IL 12p70 produced by the DC after stimulation by the combination of one of these antibodies with sCD40L and IFN-γ will be enhanced compared to the level induced by sCD40L and IFN-γ alone. Apart from synergism between sCD40L and an anti-CD40 antibody, two anti-CD40 antibodies may also show synergism with each other in the induction of IL-12p70 secretion. This synergism may occur most noticeably between antibodies that block binding of sCD40L to CD40 and those that are partial or non-inhibitors of this interaction, as these antibodies are expected to bind different epitopes on CD40.

In analogy to the experiment in which the maturation of DC was tested, the effect on CTL activation of the anti-CD40 antibody samples, used on their own or together with sCD40L, will be evaluated in future experiments. It is expected that, resulting from more efficient stimulation of the DC, synergism in CTL activation will occur between the same combinations of sCD40L and monoclonal antibodies as in the maturation assay. The same holds true with regard to synergism in CTL activation between two different anti-CD40 antibodies.

Example 6

Enhanced Potency, in Comparison to CD40 Agonist Antibody, of a Bispecific Antibody Directed to CD40 and 4-1BB Ligand or a Bispecific Antibody Directed to CD40 and CD28 in the Ability to License DC for CTL Activation Use of a bi-specific antibody with specificity for CD40 on one side and a determinant on T cells on the other side potentially has the benefit of bringing the activated DC in close contact with surrounding T cells. If the antibody part that recognizes the T cell determinant has agonistic properties, the additional benefit may be that the attracted T cell will be stimulated both through the signals delivered by the activated DC and the agonistic properties of the T cell part of the bispecific antibody. This possibility will be evaluated by comparing the effect of the addition of the CD40 monoclonal antibodies and the bispecific antibodies in the above described DC-CTL co-culture system, using flu peptide specific CD8+ T cell responses as read out.

The description and examples are exemplarily only and not limiting, and the invention is defined only by the claims which follow, and includes all equivalents, known and unknown, of such claimed subject matter.

What is claimed is:

1. A gene construct coding for an anti-CD40 monoclonal antibody, wherein said anti-CD40 antibody is produced by a hybridoma selected from the group consisting of hybridomas deposited with American Type Culture Collection (ATCC) as deposit designation PTA-2993, PTA-2994, PTA-2995, PTA-2996, PTA-2997, PTA-2998 and PTA-2999.

2. A gene construct coding for a fragment, of an anti-CD40 antibody produced by a hybridoma selected from the group consisting of hybridomas deposited with American Type Culture Collection (ATCC) as deposit designation PTA-2993, PTA-2994, PTA-2995, PTA-2996, PTA-2997, PTA-2998 and PTA-2999.

3. A cell transfected with a gene construct according to claim 1.

4. A cell transfected with a gene construct according to claim 2.

5. The gene construct of claim 1 or 2, wherein the anti-CD40 antibody is a chimeric, humanized, Deimmunised™, or human antibody.

6. A cell transfected with the gene construct of claim 5.

* * * * *

UNITED STATES PATENT AND TRADEMARK OFFICE
CERTIFICATE OF CORRECTION

PATENT NO. : 7,820,807 B2
APPLICATION NO. : 12/420481
DATED : October 26, 2010
INVENTOR(S) : Thomas et al.

Page 1 of 1

It is certified that error appears in the above-identified patent and that said Letters Patent is hereby corrected as shown below:

ON THE TITLE PAGE:

Assignee:

Now reads:     "Pangenetics BV, Ultrecht (NL)"

Should read:   -- Pangenetics BV, Utrecht (NL) --

Signed and Sealed this
Sixteenth Day of August, 2011

David J. Kappos
*Director of the United States Patent and Trademark Office*